United States Patent [19]
Yerkovich et al.

[11] Patent Number: 5,872,497
[45] Date of Patent: Feb. 16, 1999

[54] HIGH ENERGY TRANSFER RELAY

[75] Inventors: Daniel Yerkovich, Snohomish; Stephen T. Vincent, Redmond; Richard J. Cardin, Duvall, all of Wash.

[73] Assignee: Physio-Control Corporation, Redmond, Wash.

[21] Appl. No.: 735,728

[22] Filed: Oct. 23, 1996

[51] Int. Cl.⁶ ................................................... H01H 51/22
[52] U.S. Cl. .......................... 335/78; 335/128; 335/203; 335/276
[58] Field of Search .................................... 335/128, 203, 335/270–276, 78–86

[56] References Cited

U.S. PATENT DOCUMENTS

| | | |
|---|---|---|
| 3,096,412 | 7/1963 | Martin . |
| 3,308,407 | 3/1967 | Lake . |
| 3,814,105 | 6/1974 | Howard et al. . |
| 4,460,881 | 7/1984 | Meister et al. . |
| 4,740,769 | 4/1988 | Mitschik . |
| 4,792,776 | 12/1988 | Lueneburger . |
| 4,857,872 | 8/1989 | Bassino . |
| 4,870,378 | 9/1989 | Biehl et al. . |
| 4,937,544 | 6/1990 | Mueller . |
| 4,956,623 | 9/1990 | Rolf-Dieter . |
| 4,958,137 | 9/1990 | Schroeder . |
| 5,095,294 | 3/1992 | Chikira et al. . |
| 5,151,675 | 9/1992 | Biehl et al. . |
| 5,222,492 | 6/1993 | Morgan et al. . |
| 5,339,059 | 8/1994 | Kawamura et al. . |

FOREIGN PATENT DOCUMENTS

| | | |
|---|---|---|
| 0 281 384 A2 | 7/1988 | European Pat. Off. . |
| 1.271.803 | 1/1962 | France . |
| 1.275.365 | 3/1962 | France . |
| 25 15 890 A1 | 10/1976 | Germany . |
| 2 233 824 | 1/1991 | United Kingdom . |

*Primary Examiner*—Lincoln Donovan
*Assistant Examiner*—Raymond Barrera
*Attorney, Agent, or Firm*—Christensen O'Connor Johnson Kindness PLLC

[57] ABSTRACT

A high energy transfer relay includes a housing, a solenoid, a pivot arm, a stationary contact, a switching contact and a leaf spring. The switching contact is mounted on the leaf spring. The armature of the solenoid is coupled to the pivot arm such that when the solenoid is energized, the pivot arm moves in the direction of the stationary contact. Movement is against the force of the leaf spring which is positioned to bias the pivot arm away from the stationary contact against a stop. The leaf spring also pre-loads the pivot point. In addition, the resilience of the leaf spring cushions the impact of the switching contact on the stationary contact to help prevent contact bounce. The outer end of the pivot arm includes a flat that coacts with a flat wall to form an air cushion. The air cushion also assists in preventing contact bounce by absorbing the momentum of the pivot arm after the contacts mate. Additionally, the moment of inertia of the pivot arm and associated elements located on the switching contact side of the pivot point is counterbalanced by the moment of inertia of the armature and the part of the pivot arm on the solenoid side of the pivot point. Balancing the moments of inertia ensures that an acceleration force applied to the solenoid side of the pivot point will be counterbalanced by an equal and opposite force on the switching contact side of the pivot point.

19 Claims, 4 Drawing Sheets

HIGH ENERGY TRANSFER RELAY

FIELD OF THE INVENTION

This invention relates to electrical power relays and more particularly to high energy electrical power transfer relays.

BACKGROUND OF THE INVENTION

While, as will be better understood from the following description, the present invention was developed for use in cardiac defibrillators, it is to be understood that the invention may also find use in other environments where the transfer of high energy electric power is required.

One of the most common and life-threatening medical conditions is ventricular fibrillation. A human heart experiencing ventricular fibrillation is unable to pump the volume of blood required by the human body. Loss of blood flow quickly leads to serious brain damage. Death will invariably result unless a normal heart rhythm can be restored within a short period of time. Ventricular fibrillation can result from a heart attack, or be caused by accidental electric shock or severe stress of the type that can accompany surgery, drowning or the like.

The usual way of restoring a normal rhythm to a heart experiencing ventricular fibrillation is to apply a strong electric pulse to the heart using an external cardiac defibrillator. External cardiac defibrillators have been successfully used for many years in hospitals by doctors and nurses and in the field by emergency treatment personnel, i.e., paramedics.

Conventional external cardiac defibrillators first accumulate a high energy electric charge on a storage capacitor. When a switching mechanism is closed, the stored energy is transferred in the form of a large current pulse to a pair of electrodes positioned on the chest of a patient. The switching mechanism used in most contemporary defibrillators is a heavy duty electro-mechanical relay, in many instances a rotary relay. A discharge control signal causes the relay to complete an electrical circuit between the storage capacitor and a wave shaping circuit whose output is connected to the electrodes attached to the patient.

Although the relays previously used in cardiac defibrillators have performed satisfactorily, they have a variety of disadvantages. The major disadvantage is cost. More specifically, prior art rotary relays used in external cardiac defibrillators have had high part counts, making them expensive to manufacture. Not only are the parts expensive to manufacture, they require a large amount of assembly and adjustment time. Further, prior art cardiac defibrillator high energy transfer relays have been designed such that the entire relay must be replaced even if only a small part fails, making replacement expensive. The second disadvantage is the size and weight of prior art cardiac defibrillator high energy relays. Because most external cardiac defibrillators are intended to be portable, they should be small in size and weight. Size and weight are functions of the parts used to make cardiac defibrillators. Because prior art high energy transfer relays used in portable cardiac defibrillators have been large and heavy, previously developed portable cardiac defibrillators have been heavier than desired. The weight and size of the rotary relays previously used in external cardiac defibrillators have made such relays difficult to mount, particularly on circuit boards. One way to overcome the cost, size and weight disadvantages of the high energy relays presently used in cardiac defibrillators is to use linear solenoid relays. Unfortunately, in the past, linear solenoid relays have had a number of disadvantages that have made them unsuitable for use as high energy transfer relays in cardiac defibrillators.

When a relay is closed, a switching contact is moved into engagement with a stationary contact. In the past, the contacts of both rotary and linear solenoid relays have had little resiliency and because the switching contact is moving at a high rate of speed, the momentum of the switching contact causes the switching contact to bounce away from the stationary contact after initial engagement. The bounce energy is offset by the relay closure energy, which brings the contacts back into engagement, causing a second smaller bounce and the cycle to be repeated. The switching contact bounces transiently against the stationary contact for a period of time before settling down. Arcing across the contacts occurs as the contacts bounce. Arcing has three undesirable effects. First, arcing may distort the shape of the current pulse applied to patient. Second, arcing may cause contact pitting, contact burning, or may weld the contacts together. Third, arcing can cause electromagnetic interference (EMI), which can be detrimental to the signals used by nearby control circuits.

The major disadvantage weighing against the use of linear solenoid relays in external cardiac defibrillators is inadvertent discharge of the storage capacitor. Most external defibrillators are portable and used by rescue personnel, such as fire and ambulance personnel. During transportation, defibrillators are subject to numerous shocks or jars that could cause the contacts of a linear solenoid relay to close and, thus, the associated storage capacitor to discharge. The inadvertent production of a high energy current pulse can create a hazard for rescue personnel.

The present invention is directed to providing a linear solenoid high energy transfer relay that overcomes the foregoing and other disadvantages, making it ideally suited for use in external cardiac defibrillators.

SUMMARY OF THE INVENTION

In accordance with the present invention, a linear solenoid relay ideally suited for use in a cardiac defibrillator to transfer high energy cardiac defibrillation pulses to a pair of electrodes placed on a patient is provided. The relay includes six main parts: a housing, a linear solenoid, a pivot arm, a stationary contact, a switching contact and a retraction spring. The linear solenoid, pivot arm, stationary contact and retraction spring are mounted in the housing. The linear solenoid includes an armature that is coupled to the pivot arm. The pivot arm and solenoid are mounted such that when the coil of the linear solenoid is energized, the armature moves the arm toward the stationary contact. The retraction spring is positioned so as to create a counteracting force that moves the pivot arm away from the stationary contact. The switching contact is resiliently mounted on the pivot arm in alignment with the stationary contact. When the switching contact is moved into engagement with the stationary contact, the resilient mounting absorbs some of the engagement shock thereby decreasing contact bounce.

In accordance with other aspects of this invention, the retraction spring is a leaf spring having one end that includes a terminal suitable for connection to an electric circuit. Further, the switching contact is mounted on the leaf spring, whereby the leaf spring forms the resilient mount for the switching contact.

In accordance with further aspects of this invention, the switching contact is located inwardly from the outer end of one side of the pivot arm. The region between the switching contact and the end of the pivot arm is flat. Further, located in the housing adjacent to the stationary contact is a flat wall. The flat regions of the pivot arm and the wall are positioned such that they face one another when the switching contact is moved toward the stationary contact. The flat regions of the pivot arm and the wall create an air cushion that assists in absorbing the momentum of the pivot arm and the switching contact after the switching and stationary contacts are brought together to further decrease contact bounce.

In accordance with still further aspects of this invention, the moment arm of the pivot arm and associated elements located on the switching contact side of the pivot point is counterbalanced by the moment arm of the armature of the solenoid and the part of the pivot arm on the solenoid side of the pivot point. This balancing creates equal moments of inertia on both sides of the pivot. Balancing the moment of inertia of the pivot arm on the switching control side with the moment of inertia on the solenoid side ensures that when an acceleration force is applied to the armature and the part of the pivot arm on the solenoid side of the pivot point, an equal and opposite force is applied to the switching contact side of the pivot arm. The counterbalancing minimizes movement of the armature and, thus, the pivot arm if the product incorporating the relay, i.e., the cardiac defibrillator, experiences a sudden large change in acceleration by being dropped, for example.

In accordance with yet other aspects of this invention, the housing is sized and shaped to be mounted on a printed circuit board (PCB) such that the PCB encloses one side of the housing.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 5 is an isometric view of the stationary contact of the high energy transfer relay shown in FIGS. 1–4.

DETAILED DESCRIPTION OF THE PREFERRED EMBODIMENT

The present invention is a high energy transfer relay ideally suited for use in a cardiac defibrillator. While developed for use in a portable cardiac defibrillator, as noted above, high energy transfer relays formed in accordance with this invention also find use in other products.

Figure 1:
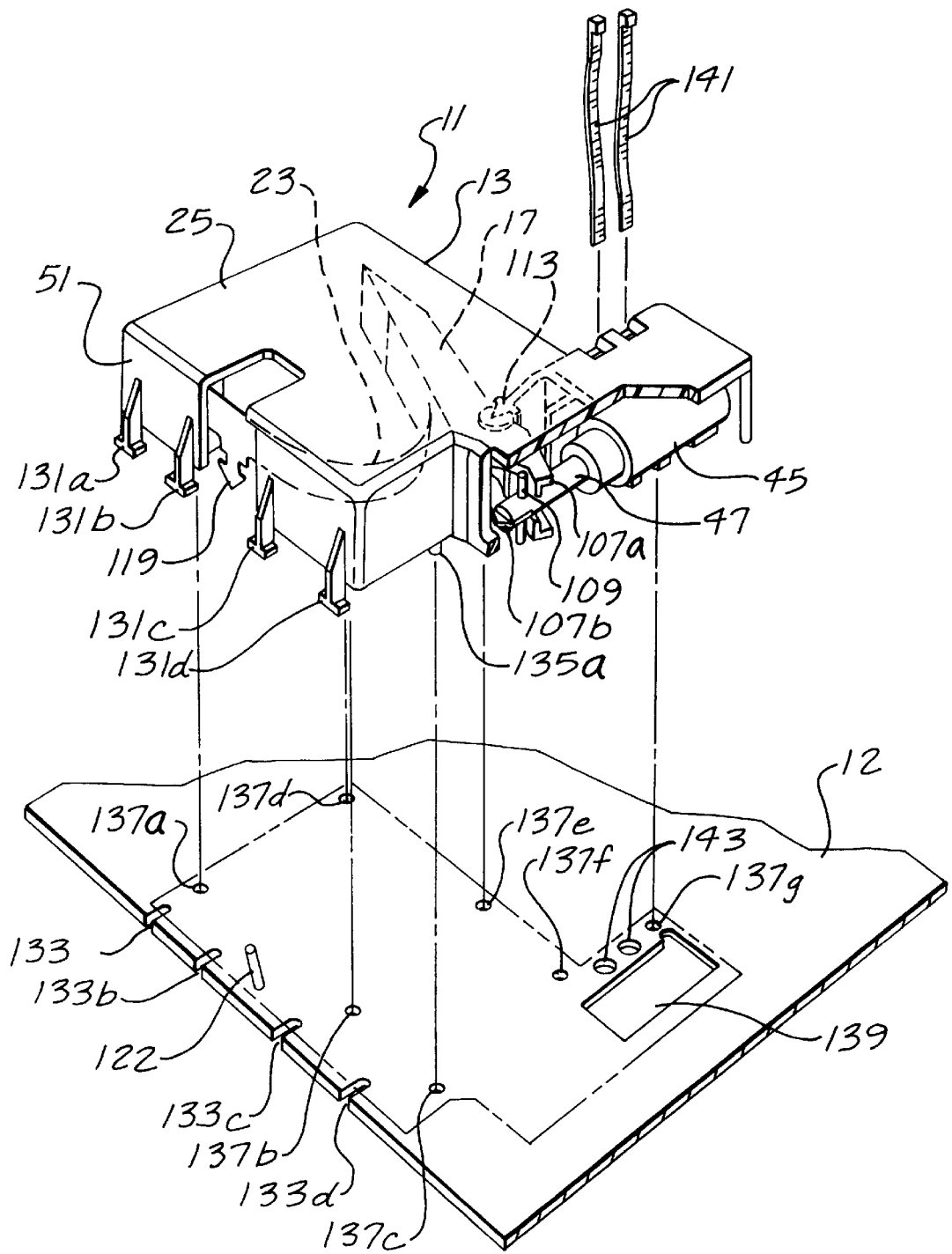
FIG. 1 is an exploded isometric view of a high energy transfer relay formed in accordance with this invention mounted on a printed circuit board (PCB)

FIG. 1 illustrates a high energy transfer relay 11 positioned on a printed circuit board (PCB) 12. As will be better understood from the following description, the housing 13 of the high energy transfer relay includes protrusions that allow the relay to be positioned and affixed to the PCB 12. As also will be better understood from the following description, the housing has an open side that is enclosed by the PCB 12.

Figure 2:
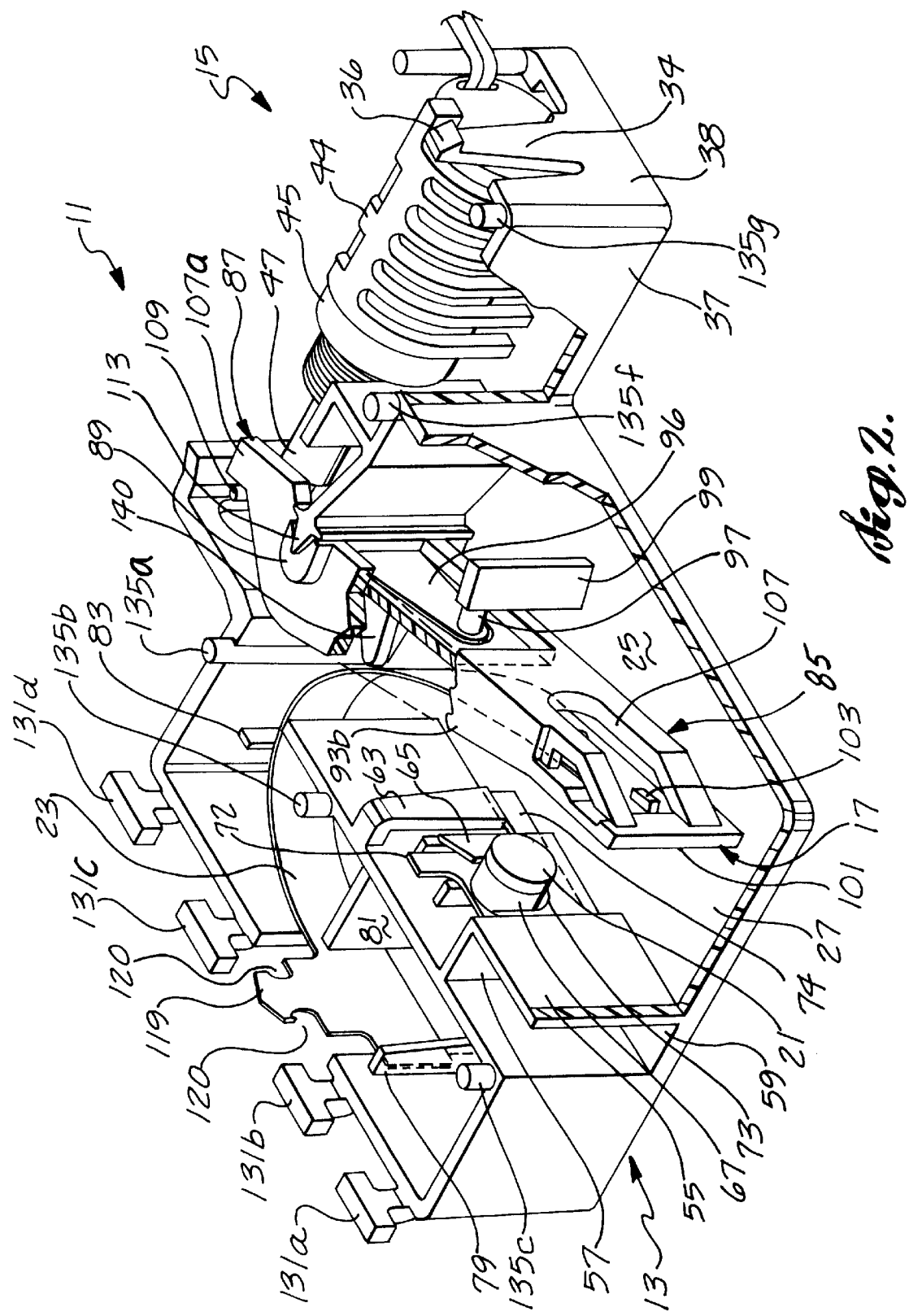
FIG. 2 is an isometric view of the high energy transfer relay shown in FIG. 1, inverted so that all of the relay elements can be seen.
Figure 3:
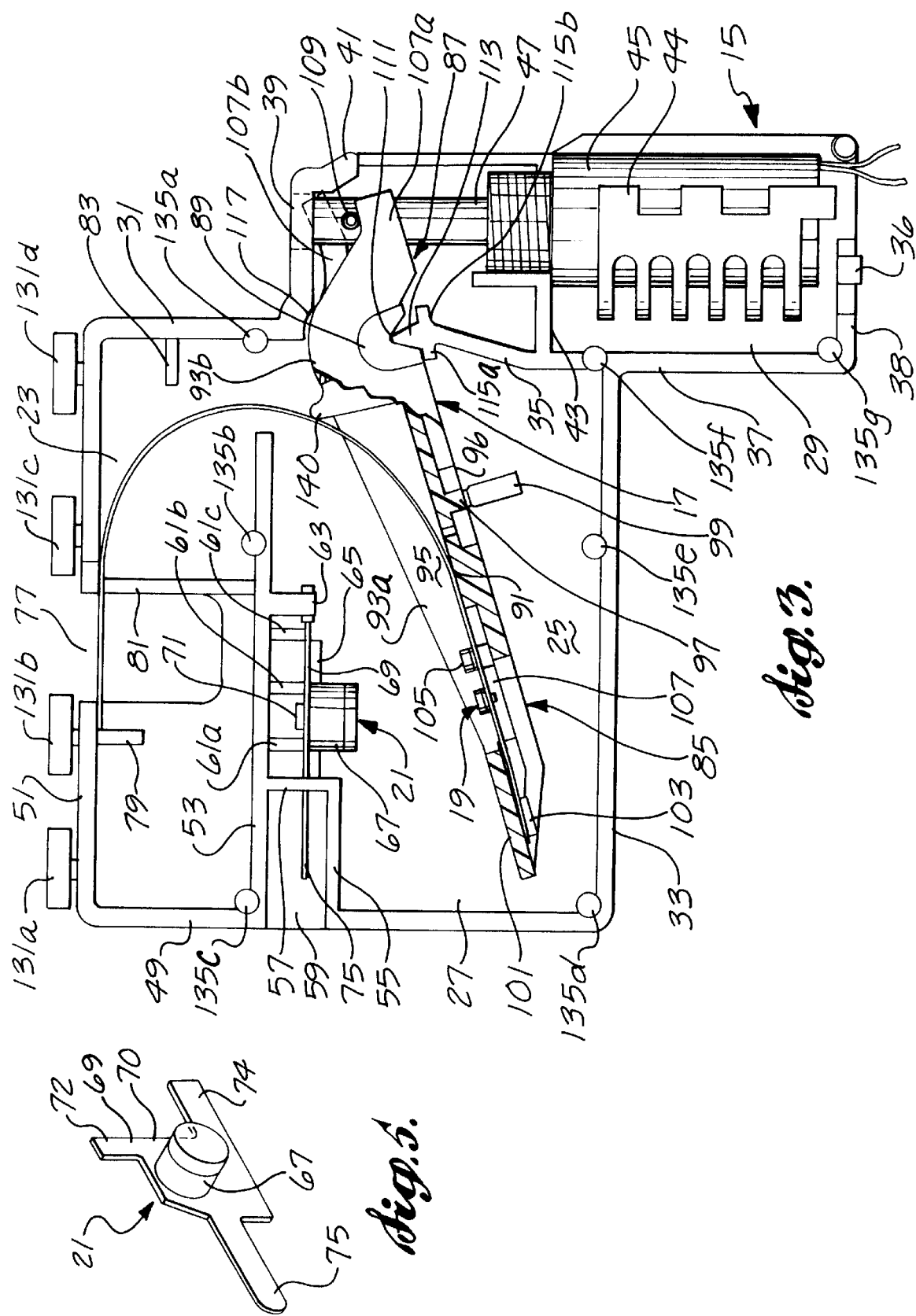
FIG. 3 is a plan view, partially in section, of the high energy transfer relay of FIGS. 1 and 2 showing the relaying contacts in the open position.
Figure 4:
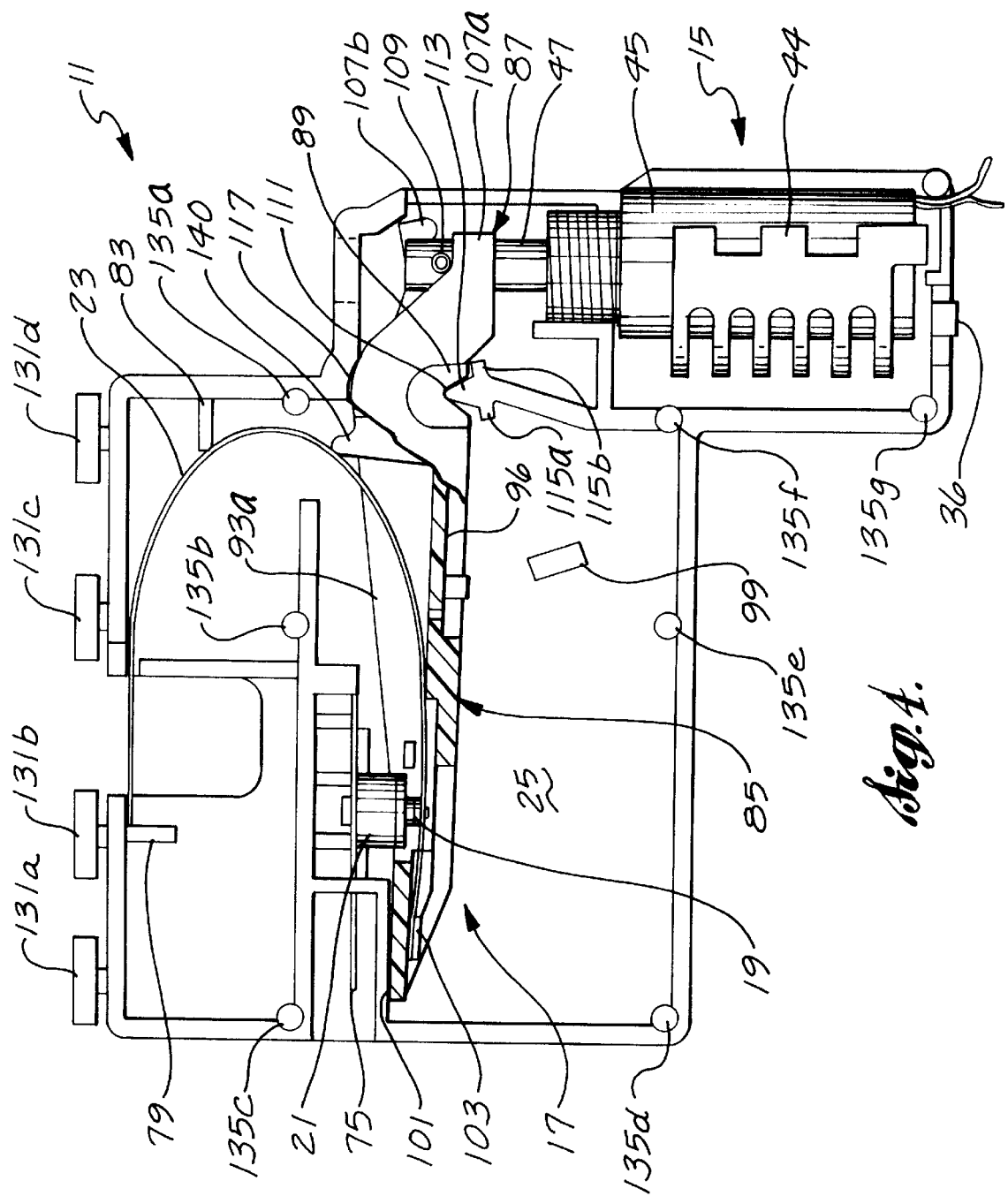
FIG. 4 is a plan view, partially in section, of the high energy transfer relay of FIGS. 1 and 2 showing the relay contacts in the closed position.

As shown in FIGS. 2–4, in addition to the housing, the major elements of a high energy transfer relay 11 formed in accordance with this invention include a solenoid 15, a pivot arm 17, a switching contact 19, a stationary contact 21 and a retraction spring 23. The housing 13 includes a base wall 25 and a plurality of peripheral and interior walls that extend outwardly from one side of the base wall. Preferably the base wall 25 and the plurality of peripheral and interior walls are molded from a suitable, clear, insulative material, i.e., a suitable, clear plastic material. The use of a clear plastic material allows the relay components to be inspected without disassembly. Because the housing is molded, the base wall and the plurality of peripheral and interior walls are integral with one another. As will be better understood from the following description, the base wall 25 and the plurality of peripheral and interior walls generally define two chambers—a pivot arm/contact chamber 27 and a solenoid chamber 29. Both the pivot arm/contact chamber 27 and the solenoid chamber 29 have a rectangular shape. The use of a clear plastic material allows components housed in the chambers to be inspected without opening the housing after it has been mounted on a printed circuit board in the manner illustrated in FIG. 1 and described more fully below.

The solenoid chamber 29 begins near the center of the first peripheral wall 31 of the four peripheral walls that define the pivot arm/contact chamber 27 and extends outwardly along the related side of the pivot arm/contact chamber 27, past the second peripheral wall 33 of the pivot arm/contact chamber. Thus, the solenoid chamber 29 forms a protrusion that extends outwardly from the pivot arm/contact chamber 27. An interior wall 35 common to both chambers lies between the solenoid chamber 29 and the pivot arm/contact chamber 27. The interior wall 35 merges into an outwardly extending peripheral wall 37 of the solenoid chamber 29. The outwardly extending peripheral wall 37 merges into a short wall 38 located transverse to the outwardly extending peripheral wall 37. The short wall includes a latch arm 34. The latch arm 34 includes a hook 36 that assists in attaching the housing 13 to the PCB 12.

The solenoid chamber 29 includes a further peripheral wall 39 that extends outwardly from the first peripheral wall 31 of the pivot arm/contact chamber 25. The further peripheral wall 39 of the solenoid chamber merges into a finger 41 that defines a short section of the remaining wall of the solenoid chamber 29. The remaining portions of the sides of the solenoid chamber defined by the short wall 38 and the finger 41 are open. Extending into the solenoid chamber 29 from the common interior wall 35 is an L-shaped wall 43. The solenoid chamber includes a cage 44 integrally formed in the solenoid chamber between the L-shaped wall 43 and the short peripheral wall 38.

The solenoid 15 is a linear solenoid comprised of a coil 45 and an armature 47. The coil 45 is sized to fit in the cage 44 and, thus, lies between the L-shaped wall 43 and the short wall 38. The armature 47 extends outwardly from the coil 45 toward the further peripheral wall 39 of the solenoid chamber 29. Further, the coil includes a shoulder that abuts the L-shaped wall 43.

In contrast to the solenoid chamber 29, the remaining sides of the pivot arm/contact chamber 27 are enclosed by third and fourth peripheral walls 49 and 51. The third peripheral wall 49 lies parallel to the first peripheral wall 31 and the fourth peripheral wall 51 lies parallel to the third peripheral wall 33. Extending inwardly from the third peripheral wall 49 of the pivot arm/contact chamber 27 is a long interior wall 53 and a short interior wall 55. The long and short interior walls 53 and 55 lie substantially parallel to one another and substantially parallel to the second and fourth peripheral walls 33 and 51. A cross wall 57 extends between the inner end of the short interior wall 55 and the long interior wall 53. The cross wall 57, the short interior wall 55 and the portion of the long interior wall 53 up to the intersection with the cross wall 57 define a connection chamber 59 that is open to the outside of the housing 13.

Extending outwardly from the long interior wall 53, parallel to the cross wall 57 are three thin walls 61a, 61b and 61c and a downwardly extending hook 63. The hook 63 extends outwardly slightly beyond the ends of the thin walls 61a, 61b and 61c. Extending inwardly from the cross wall 57 is a slotted wall 65. The slotted wall is spaced from the thin walls 61a, 61b and 61c by a small distance.

As shown in FIG. 5, the stationary contact 21 includes a cylindrical button 67 and a connector plate 69, preferably formed of beryllium copper. A rivet 71 or other suitable device affixes the button 67 to one side of the connector plate 69. Preferably, the button is formed of two or more layers. The outer layer is formed of silver/cadmium oxide. The inner layer(s) are formed of copper having a protrusion that extends through a hole in the connector plate 69 and is swaged to form the rivet 71 and affix the button 67 to the connector plate 69. The diameter of the button 67 is slightly less than the distance between the walls of a U-shaped slot 73 formed in the slotted wall 65.

The connection plate 69 includes a main body 70 to which the cylindrical button is attached. Extending outwardly from the body are three fingers 72, 74 and 75. The thickness of the connector plate 69 is substantially the same in the distance between the thin walls 61a, 61b, and 61c and the slotted wall 65. As a result, the connector plate can be slid between the thin walls 61a, 61b and 61c and the slotted wall 65. During installation, the button 67 is slid into the slot 73 in the slotted wall 65; the first finger 72 extends upwardly as viewed in FIGS. 2–4; the second finger 74 pushes the hook 63 inwardly until the second finger 74 drops below the hook 63; and the third finger 75 passes through a slit in the cross wall 57. The action of the hook 63 locks the stationary contact 21 in place. When correctly positioned, the third finger 75 extends into the connection chamber 59 and forms a terminal for connection to a source of power. The first finger 72 presses against the PCB 12 shown in FIG. 1. This helps to hold the connector plate 69 in place in the event the hook 63 becomes disengaged.

The fourth peripheral wall 51 of the pivot arm/contact chamber 27 includes an aperture 77. Extending inwardly from the portion of the fourth peripheral wall 51 integral with the third peripheral wall 49 is a spring stop wall 79. The spring stop wall 79 is spaced a small distance away from one edge of the aperture 77. Extending outwardly from the long interior wall 53, toward the other edge of the aperture 77 is a long spring retention wall 81. The outer edge of the long spring retention wall 81 is spaced from the other peripheral wall 51 of the pivot arm/contact chamber 27 by a small distance. Extending inwardly from the first peripheral wall 31 of the pivot arm/contact chamber 27 is a short spring retention wall 83.

The pivot arm 17 is formed of an insulation material, i.e., a plastic, molded or formed into a shape that performs several functions, described below. The pivot arm includes a long leg 85 and a short leg 87. The long leg of the pivot arm includes a main web 91 that lies orthogonal to the base wall 25 of the housing 13. Integrally formed along the upper and lower edges of the main web 91 are a pair of orthogonally oriented flanges 93a and 93b. The main web 91 and the flanges 93a and 93b define a slot 95 in the long leg 85 of the pivot arm 17. The slot 95 faces the stationary contact 21.

Formed in the main web 91 is a spring arm 96. Extending outwardly from the tip of the spring arm 96 on the side of the pivot arm 17 remote from the slot 95 is a small protrusion 97. The small protrusion 97 is sized and positioned to impinge on a stop 99 when the pivot arm 17 is in the retracted position shown in FIGS. 2 and 3 and described below. The stop 99 is integral with and projects outwardly from the base wall 25, near the corner between the interior wall 35 that is common to both the pivot arm/contact chamber 27 and the solenoid chamber 29, and the second peripheral wall 33 of the pivot arm/contact chamber 27. The spring arm 96 and the stop 99 form a sprung stop that isolates the pivot arm 17 from impact energy applied to the housing 13.

Located on the outer end of the long side 85 of the pivot arm 17 is flat 101. The flat 101 is located at the outer end of the slot 95 and faces the short interior wall 55. An aperture 107 is located between the flat 101 and the outer end of the main web 91 of the pivot arm 17.

Integrally formed on the side of the flat 101 remote from the side facing the short interior wall 55 is a spring alignment protrusion 103. Integrally formed on the side of the main web 91 facing the stationary contact, near the outer end thereof, are two L-shaped spring capture elements 105. The L-shaped spring capture elements protrude outwardly from the flanges 93a and 93b and face one another.

The short side 87 of the pivot arm 17 has the shape of a yoke, i.e., includes two arms 107a. The arms 107a lie in the plane of the flanges 93a and 93b and on either side of the armature 47 of the solenoid 15. Located between the two arms 107a is a center arm 107b. The center arm 107b is offset beyond the two arms 107a, along the longitudinal axis of armature 47. As shown in FIG. 1, the center arm 107b is positioned to extend into a slot located at the end of the armature 47. A pin 109 extends through the armature 47 such that the two arms 107a lie on one side of the pin 109 and the center arm 107b lies on the other side of the pin 109. Thus the two arms 107a, the center arm 107b and the pin 109 affix the short side of the pivot arm 87 to the armature 47.

The pivot point 89 of the pivot arm 17 is defined by an indentation 111 formed in the pivot arm 17 between the long and short sides 85 and 87. The indentation 111 lies on the same side of the pivot arm 17 as the protrusion 97 and the stop 99. The indentation 111 co-acts with the end 113 of the common interior wall 35 that lies between the pivot arm/contact chamber 27 and the solenoid chamber 29. The end 113 has an arrowhead shape. More specifically, the arrowhead shaped end 113 defines one side of a gap in the common interior wall 35 through which the pivot arm 17 passes. The inner end of the arrowhead shape is defined by a pair of outwardly extending flanges 115a and 115b. The other side of the gap in the common interior wall 35 is defined by the junction between the first peripheral wall 31 of the pivot arm/contact chamber 27 and the further peripheral wall 39 of the solenoid chamber. This junction includes a curved section 117 that mates with a curved section formed in the outer edges of the flanges 93a and 93b of the pivot arm 17. The center of the radius of curvature of the curved section is the tip of the arrowhead-shaped end 113 of the common wall 35, which is the center of rotation of the pivot arm 17.

The retraction spring 23 is a leaf spring that extends between the spring stop wall 79 that extends inwardly from the fourth peripheral wall 51 of the pivot arm/contact chamber 27 and the spring alignment protrusion 103 integrally formed on the pivot arm 17. More specifically, starting at the spring stop wall 79, the retraction spring 23 passes through the slot between the outer edge of the long retention wall 81 and the fourth peripheral wall 51 of the pivot arm/contact chamber 27. Next, the retention spring curves past the short spring retention wall 83 and the inner end of the long interior wall 53. The retraction spring 23 then enters the slot 95 in the pivot arm 17, passing a finger 140 that extends outwardly from the web 91. The spring passes through the slots defined by the L-shaped spring capture elements 105 and the web 91 of the pivot arm 17. The retention spring ends at the spring alignment protrusion 103, which slides into a slot formed in the end of the retraction spring 23.

As will be better understood from the following description of the operation of the invention, the short spring retention wall 83 improves the spring rate. As the relay closes, the spring force starts out weak. As the force produced by the solenoid 15 increases, the force of the retraction spring 23 increases as the retraction spring 23 comes in contact with the short spring retention wall 83. In essence, the shape changes from a large radius curve to two shorter curves joined by a short flat section.

The portion of the retraction spring 23 that spans the aperture 77 in the other peripheral wall 51 of the pivot arm/contact chamber 27 includes an arrowhead shaped protrusion 119. Latching slots 120 are located inwardly from the triangular shaped end of the arrowhead shaped protrusion 119. The arrowhead shaped protrusion 119 forms a male terminal suitable for insertion into a slot 122 located in a PCB 12, as shown in FIG. 1.

The switching contact 19 is mounted on the side of the retraction spring 23 that faces the stationary contact 21. The switching contact 19 is aligned with the gap 107 between the flat 101 and the outer edge of the web 91 of the pivot arm 17. This position is such that the switching contact 19 impinges on the stationary contact 21 when the relay is almost closed, as shown in FIG. 4 and described below. As with the stationary contact, preferably the switching contact 19 is a copper button having an outer layer formed of silver/cadmium oxide.

Turning now to the operation of the high energy transfer relay 11 shown in the drawings, when the solenoid coil 45 is unenergized, the retraction spring 23 rotates the pivot arm 17 such that the switching contact 19 is moved away from the stationary contact 21. In the fully retracted position, the protrusion 97 rests against the stop 99. When the solenoid coil 45 is energized, the armature 47 is pulled into the solenoid coil 45, causing the pivot arm 17 to rotate about the pivot point 111, against the force created by the retraction spring 23. Continued movement brings the switching contact 19 into contact with the stationary contact 21, allowing power to be transferred through the contacts.

The high energy transfer relay shown in the drawings includes two anti-bounce mechanisms. One is formed by the resilience of the retraction spring 23 and the other is formed by the short interior wall 55 and the flat 101 of the pivot arm 17.

The anti-bounce mechanism provided by the resilience of the retraction spring 23 is best shown in FIG. 4. Just before the flat 101 engages the short interior wall 55, the switching contact 19 engages the stationary contact 21. When this occurs, the resilience of the retraction spring 23 causes the switching contact 19 to move toward the aperture 107 in the pivot arm 17. As a result, a "hard" contact impact is turned into a soft contact impact, which absorbs some of the momentum of the pivot arm 17.

The anti-bounce mechanism provided by the short interior wall 55 and the flat 101 results from trapping air between these two surfaces as the pivot arm is move into the contact closed position. The force needed to push the air out from between these two surfaces as the switching contact 19 is moved into engagement with the stationary contact 21 absorbs some of the momentum energy stored in the moving pivot arm 17. A further anti-bounce effect occurs after the surfaces meet. More specifically, because it takes energy to pull air back into the area between the flat 101 and the short interior wall 55 after these surfaces meet, the momentum energy created by the bounce force is spent by air suction rather than pivot arm movement. This air cushion-suction in effect removes momentum energy that would otherwise cause the pivot arm 17 and, thus, the contacts 19 and 21 to bounce.

The air cushion-suction effect, plus the momentum absorption effect provided by the resilience of the retraction spring 23, minimizes contact bounce and allows the switching contact 19 to remain in engagement with the stationary contact 21 for a period adequate for completion of a high energy pulse to pass between the contacts. Thereafter, the relay closed control signal is removed from the solenoid coil 45 releasing the armature 47. When this occurs, the retraction spring 23 rotates the pivot arm 17 such that the switching contact 19 is moved away from the stationary contact 21. The pivot arm 17 ultimately assumes the retracted position illustrated in FIGS. 2 and 3.

The sizing of the pivot arm 17 and the armature 47 of the present invention are such that the moment arm of the long side 85 of the pivot arm 17 counterbalances the moment arm of the armature 47 and the moment arm of the short side 87 of the pivot arm 17. As a result rapid movement of the armature 47 in the appropriate direction, i.e., acceleration of the armature 47 along the longitudinal axis of the armature 47 in the direction of the coil 45, is opposed by an equal and opposite force applied to the long side 85 of the pivot arm 17. Thus, armature 47 and short side 87 moment arm acceleration is counteracted by the long side 85 of the pivot arm moment arm, because the moment of inertias are equal. As a result, the pivot arm 17 remains substantially stationary, whereby inadvertent contact engagement is eliminated.

As shown in FIG. 1, the housing 13 is mounted in the PCB 12 by sliding a plurality of T-shaped protrusions 131a, 131b, 131c and 131d located along the edge of the fourth wall 51 of the housing 13 into a plurality of slots 133a, 133b, 133c and 133d located along one edge of the PCB 12. A plurality of protruding pins 135a, 135b, 135c . . . located along the edges of selected walls of the housing 13 slide into corresponding holes 137a, 137b, 137c . . . in the PCB 12. When suitably positioned, the hook 36 located on the end of the latch arm 34 engages the edge of a suitably positioned hole 139 in the PCB 12 to latch the housing 13 to the PCB. Then two wire ties 141 that pass through additional holes 143 in the PCB 12 more permanently attach the housing 13 to the PCB 12.

In addition to the advantages alluded to above, high energy transfer relays formed in accordance with this invention have a number of additional advantages. Such relays are more reliable than prior designs because they include fewer parts. In addition to improved reliability, fewer parts have three additional advantages: (1) reduction in assembly time; (2) reduction in cost; and (3) wiring simplification. Assembly reductions occur because high energy transfer relays formed in accordance with the invention: (1) permit end item assembly instead of requiring a separate assembly line; (2) eliminate separate component testing; (3) avoid the need to design special assembly fixtures; and (4) eliminate the need for adjustment after assembly. In addition, the repair of high energy transfer relays formed in accordance with the invention is inexpensive because only the failed parts need to be replaced rather than the entire relay.

The invention has a number of features and advantages that may not be readily understood from the previous description. First, the switching contact 19 is sprung separately from the mass of the pivot arm 17. This allows the switching and stationary contacts to engage before the air cushion absorbs the momentum of the pivot arm 17 and remain engaged as the momentum is absorbed. This allows rapid contact engagement, which reduces arcing, with minimum contact bounce. In addition to this function, the retraction spring 23 performs at least four additional functions. The retraction spring 23 holds the pivot arm 17 in place without slop. The use of a pin to perform this function, for example, would result in slop, i.e., extraneous movement, particularly after extended use. The retraction spring 23 also conducts current to the switching contact. The retraction spring 23 also makes contact with the PCB 12. No separate wiring is required. Assembly is assisted by the insertion of the arrowhead-shaped protrusion 119 into a canted slot 122 in the PCB 12. Finally, the retraction spring 23 provides the pivot arm 17 return force.

All of the parts included in the illustrated embodiment of the invention are fixtured with respect to one another. That is, the parts are latched to one another in a manner that eases assembly and avoids the need for special assembly holding fixtures. In essence, all of the parts snap fit or in some other manner engage one another and the next assembly step locks them in place.

While a preferred embodiment of the invention has been illustrated and described, it is to be understood that within the scope of the appended claims various changes can be made therein without departing from the spirit of the invention.

The embodiments of the invention in which an exclusive property or privilege is claimed are defined as follows:

1. A high energy transfer relay comprising:

a housing, including first and second chambers;

a solenoid housed in said first chamber, said solenoid including an armature and a coil around the armature;

a stationary contact mounted in said second chamber;

a pivot arm extending between said first and second chambers, the end of said pivot arm located in said first chamber being coupled to the armature of said solenoid such that the energization of said solenoid causes said armature to rotate said pivot arm about a pivot point located between said first and second chambers, wherein the end of said pivot arm located in said second chamber moves toward said stationary contact;

a leaf spring mounted in said second chamber and impinging on said pivot arm so as to move said pivot arm away from said stationary contact and against the direction of movement of said pivot arm caused by the energization of said solenoid; and a switching contact mounted on said leaf spring in a position such that when the end of said pivot arm located in said second chamber is moved toward said stationary contact by the energization of said solenoid, said switching contact rotates about said pivot point to engage said stationary contact.

2. A high energy transfer relay as claimed in claim 1 wherein said leaf spring conducts electric current to said switching contact.

3. A high energy transfer relay as claimed in claim 1 including a stop mounted in said second chamber on the opposite side of said pivot arm from said switching contact and said stationary contact for limiting the movement of said pivot arm away from said stationary contact produced by said leaf spring.

4. A high energy transfer relay as claimed in claim 1 wherein said pivot arm is coupled to said armature by a coupling mechanism that includes a yoke formed in one end of said pivot arm and a pin that extends through said armature.

5. A high energy transfer relay as claimed in claim 1 wherein the moment of inertia of the portion of said pivot arm located in said second chamber is substantially equal to the moment of inertia of said pivot arm located in said first chamber plus the moment of inertia of said armature of said solenoid.

6. A high energy transfer relay as claimed in claim 5 wherein said leaf spring conducts electric current to said switching contact.

7. A high energy transfer relay as claimed in claim 6 including a sprung stop mounted in said second chamber on the opposite side of said pivot arm from said switching contact and said stationary contact for limiting the movement of said pivot arm away from said stationary contact produced by said leaf spring.

8. A high energy transfer relay as claimed in claim 7 wherein said pivot arm is coupled to said armature by a coupling mechanism that includes a yoke formed in one end of said pivot arm and a pin that extends through said armature.

9. A high energy transfer relay as claimed in claim 1 including an interior wall located in said second chamber adjacent said stationary contact and wherein said pivot arm includes a flat region aligned with said interior wall such that said flat region and said interior wall coact to create an air cushion when said solenoid is energized to move said pivot arm toward said stationary contact and, thus, said switching contact into engagement with said stationary contact.

10. A high energy transfer relay as claimed in claim 9 wherein the moment of inertia of the portion of said pivot arm located in said second chamber is substantially equal to the moment of inertia of said pivot arm located in said first chamber plus the moment of inertia of said armature of said solenoid.

11. A high energy transfer relay as claimed in claim 10 wherein said leaf spring conducts electric current to said switching contact.

12. A high energy transfer relay as claimed in claim 11 including a stop mounted in said second chamber on the opposite side of said pivot arm from said switching contact and said stationary contact for limiting the movement of said pivot arm away from said stationary contact produced by said leaf spring.

13. A high energy transfer relay as claimed in claim 12 wherein said pivot arm is coupled to said armature by a coupling mechanism that includes a yoke formed in one end of said pivot arm and a pin that extends through said armature.

14. A high energy transfer relay as claimed in claim 1 wherein the resiliency of said leaf spring absorbs some of the energy product when said switching contact engages said stationary contact to reduce the contact bounce that occurs when said switching contact engages said stationary contact.

15. A high energy transfer relay as claimed in claim 14 including an interior wall located in said second chamber adjacent said stationary contact and wherein said pivot arm includes a flat region aligned with said interior wall such that said flat region and said interior wall coact to create an air cushion that slows down movement of the pivot arm after said stationary contact engages said switching contact.

16. A high energy transfer relay as claimed in claim 15 wherein the moment of inertia of the portion of said pivot arm located in said second chamber is substantially equal to the moment of inertia of said pivot arm located in said first chamber plus the moment of inertia of said armature of said solenoid.

17. A high energy transfer relay as claimed in claim 16 wherein said leaf spring provides an electrical conductive connection to said switching contact.

18. A high energy transfer relay as claimed in claim 17 including a sprung stop mounted in said second chamber on the opposite side of said pivot arm from said switching contact and said stationary contact for limiting the movement of said pivot arm away from said stationary contact produced by said leaf spring.

19. A high energy transfer relay as claimed in claim 18 wherein said pivot arm is coupled to said armature by a coupling mechanism that includes a yoke formed in one end of said pivot arm and a pin that extends through said armature.

* * * * *

UNITED STATES PATENT AND TRADEMARK OFFICE
CERTIFICATE OF CORRECTION

PATENT NO. : 5,872,497
DATED : February 16, 1999
INVENTOR(S) : D. Yerkovich et al.

It is certified that error appears in the above-indentified patent and that said Letters Patent is hereby corrected as shown below:

| COLUMN | LINE | |
|---|---|---|
| [57] Pg. 1, col. 2 | Abstract 13 of text | after "includes a flat" insert --area-- |
| Pg. 1, col. 2 | Attorney, Agent or Firm | "Christensen O'Connor Johnson Kindness$^{PLLC}$" should read ---Christensen O'Connor Johnson & Kindness$^{PLLC}$ -- |
| 10 (Claim 17, | 51 line 2) | "electrical" should read --electrically-- |

Signed and Sealed this

Fifth Day of October, 1999

Attest:

Q. TODD DICKINSON

*Attesting Officer*    *Acting Commissioner of Patents and Trademarks*